United States Patent

Gregorovich

[11] Patent Number: 5,571,931
[45] Date of Patent: Nov. 5, 1996

[54] PROCESS FOR THE SYNTHESIS OF VINYLDIOXO COMPOUNDS

[75] Inventor: Basil V. Gregorovich, Wilmington, Del.

[73] Assignee: E. I. Du Pont de Nemours and Company, Wilmington, Del.

[21] Appl. No.: 435,251

[22] Filed: May 5, 1995

Related U.S. Application Data

[63] Continuation of Ser. No. 186,367, Jan. 25, 1994, abandoned.

[51] Int. Cl.$^6$ .................................................. C07D 319/06
[52] U.S. Cl. ........................................................ 549/374
[58] Field of Search ............................................ 549/374

[56] References Cited

U.S. PATENT DOCUMENTS

| 3,010,918 | 11/1961 | Ikeda . | |
|---|---|---|---|
| 3,010,923 | 11/1961 | Ikeda . | |
| 3,014,924 | 12/1961 | Brachman . | |
| 3,197,484 | 7/1965 | Ikeda . | |
| 5,216,179 | 6/1993 | Hoepp et al. | 549/372 |

OTHER PUBLICATIONS

Hochberg, The chemistry of the vinyl cyclic acetals and their air drying reactions, *JOCCA* 48, 11, 1043–1068, 1965.

*Primary Examiner*—Nicky Chan
*Attorney, Agent, or Firm*—James A. Costello

[57] ABSTRACT

An improved process for preparing a vinyl-substituted dioxo compound, in which process a vinyl aldehyde is reacted with a compound having three or more hydroxyl groups. In particular, the reaction is carried out, using an acid catalyst, in an organic solvent comprising an aliphatic solvent which forms a binary azeotrope with water as the reaction is driven to completion.

6 Claims, No Drawings

PROCESS FOR THE SYNTHESIS OF VINYLDIOXO COMPOUNDS

This is a continuation of application Ser. No. 08/186,367, filed Jan. 25, 1994, now abandoned.

BACKGROUND OF THE INVENTION

This invention relates to an improved process for the synthesis of certain vinyldioxo compounds.

Vinyldioxo compounds (also referred to herein as VDO compounds).are well known. All are cyclic acetals, extensively studied and patented by Ikeda (U.S. Pat. Nos. 3,010,918; 3,010,923; 3,197,484), by Brachman(U.S. Pat. No. 3,014,924), and by others and described in detail by Hochberg (JOCCA 48, 11, 1043–1068, 1965). The simplest compounds in this class are made by a reaction of acrolein with a compound having two hydroxyl groups, either on adjacent carbon atoms or on carbon atoms separated by an additional carbon atom. When more than two hydroxyl groups are present in a compound, different pairs of hydroxyl groups can react with the aldehyde to form a cyclic acetal. Typical compounds having at least two hydroxyl groups include, for example, ethylene glycol, glycerin, 1,2,6-hexanetriol, and trimethylolpropane. Depending on the number and type of hydroxyl groups, the resulting VDO can be either a substituted 1,3-dioxolane or a substituted 1,3-dioxane, but frequently it is a mixture of a dioxolane with a dioxane. The reaction of acrolein (1) with trimethylolpropane (2) is shown below in Equation 1. The formation of VDO compounds, like other acetal-forming reactions, is catalyzed by acids.

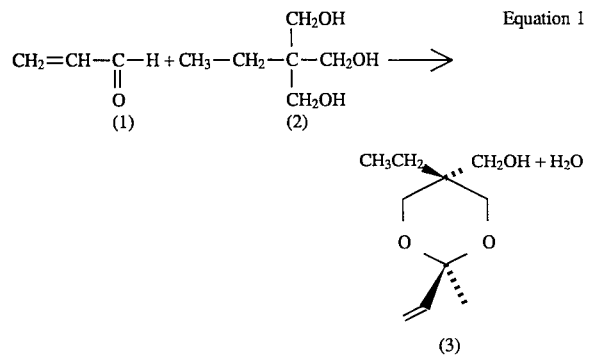

Equation 1

$$CH_2=CH-\underset{\underset{O}{\parallel}}{C}-H + CH_3-CH_2-\underset{\underset{CH_2OH}{|}}{\overset{\overset{CH_2OH}{|}}{C}}-CH_2OH \longrightarrow$$

(1)    (2)

(3)

The reaction product of formula (3) is a 2-vinyl-1,3-dioxane substituted in the 1-position with an ethyl group and with a hydroxymethyl (methylol) group.

VDO compounds and their various derivatives have been described as useful polymerizable materials, which have the potential of providing both pigmented and clear-coat finishes in automotive and other applications. Those compounds polymerize in the presence of oxygen, such reactions being catalyzed by cobalt compounds. In an aqueous medium and in the presence of acids, the VDO compounds are unstable, so that further reactions are carried out in either a neutral, an alkaline, or an organic medium. Hochberg (op. cit.) discusses various syntheses and properties of many VDO compounds. In spite of the great industrial potential of VDO compounds, they have not been successfully commercialized in high performance coatings.

Improvements in the general process for making VDO compounds have been described or patented, most recently by Hoepp et al. (U.S. Pat. No. 5,216,179). Most prior art processes give the desired cyclic acetals in yields varying from about 60% to about 90%. For environmental reasons, it is desirable to carry out the synthesis at reasonably high concentrations of starting materials, using moderate amounts of volatile solvents and avoid releasing those solvents into the atmosphere There is, therefore, a need for a process that is environmentally friendly and produces well defined, single VDO compounds in virtually quantitative yields.

SUMMARY OF THE INVENTION

According to the present invention, there is now provided an improved process for the synthesis of 1,3-dioxo compounds substituted in the 2-position with a vinyl group, said process comprising:

A) selecting a vinyl aldehyde and a compound having at least three hydroxymethyl groups in positions separated by one carbon atom and having no other hydroxyl groups in its molecule, all the hydroxymethyl groups present being strutrurally equivalent, said compound being represented by the following formula (4):

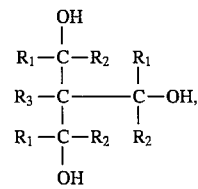

where all R 1 groups always (concurrently) have the same meaning and are selected from the group consisting of H, $CH_3$, $CH_2CH_3$, phenyl, Cl, F, and COOR;

all $R_2$ groups always (concurrently) have the same meaning and are selected from the group consisting of H, $CH_3$, $CH_2CH_3$, phenyl, Cl, F, and COOR; and $R_3$ is selected from the group consisting of H, $CH_3$, $CH_2CH_3$, phenyl, Cl, F, and COOR; and R is a substitued or unsubstituted $C_1$–$C_{20}$ (preferably $C_1$–$C_{10}$) branched, unbranched, or cyclic alkyl or a $C_6$–$C_{10}$ substituted or unsubstituted aryl group;

B) contacting together the compounds selected in step A, above, in the presence of an aromatic, hydrocarbon solvent having a boiling point of about 100°–115° C., and in the presence of an aliphatic hydrocarbon having a boiling point within the range of about 60°–100 ° C. and being capable of forming a binary azeotrope with water within this temperature range; said aliphatic hydrocarbon being present in an amount of 5–30 weight percent, based on the total of the materials recited in A above plus any aromatic hydrocarbon solvent present; and the concentration of the materials selected in step A in the solution being about 50–95 weight percent;

C) refluxing the solution in the presence of a nonvolatile acid catalyst having a $pK_a$ at room temperature in an aqueous medium of less than 5.0, either present in a solid form or on a fixed bed during the reaction or capable of being precipitated as an insoluble salt following the reaction, and removing from the solution a binary azeotrope of water with the second, aliphatic hydrocarbon added in step B above, until the reaction is substantially complete;

D) separating the acid catalyst from the liquid phase; and

E) removing any organic liquids present in the liquid phase and recovering the reaction product.

DETAILED DESCRIPTION

The preparation of dioxo compounds according to this invention involves the reaction of a vinyl aldehyde with a hydroxyl-functional compound. The dioxo compounds can suitably have 4 to 10 carbon atoms in the ring structure, resulting in a substituted dioxetane, dioxolane, dioxane, dioxepane, dioxocane, dioxonane, or dioxecane ring.

Vinyl aldehydes are characterized by the presence of a group according to the following formula (5):

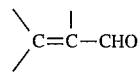

Typical vinyl aldehydes that are suitable in the process of the present invention include, for example, acrolein, methacrolein, crotonaldehyde, and cinammaldehyde.

The compound of earlier formula (4), having at least three structurally equivalent hydroxymethyl groups, as recited above, can form with a vinyl aldehyde only one cyclic acetal, which is a substituted 1,3-dioxane, as shown in the reaction illustrated by Equation 1, above. The term "structurally equivalent" means that, counting all the atoms and groups of atoms beginning with any hydroxyl groups present and ending with any other hydroxyl group present, one will always obtain the same sequence of atoms and groups of atoms. In trimethylolpropane, this sequence is as represented by the following structural formula (6):

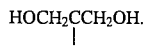

In addition to trimethylolpropane, a suitable commercially available compound having structurally equivalent hydroxymethyl groups required in the present process is trimethylolethane. Other compounds having such groups can be synthesized by methods generally known to those skilled in the art.

In the typical process of the present invention illustrated in equation 1, the aromatic hydrocarbon is not required, although one is normally used. The preferred aromatic solvent is toluene because of its boiling point of 111° C. While a lower-boiling solvent, such as benzene, could be used in principle, its high volatility and toxicity and the difficulty of separating it from the aliphatic liquid by distillation, make it impractical. Higher-boiling solvents such as xylenes could be used in principle, except that their removal from the reaction product requires a higher distillation temperature and, therefore, is not as economical.

Further, it is preferred to maintain the reaction temperature within the 60°–100° C. range because above that temperature, the reaction yield decreases significantly. While lower temperatures favor ring closure, they require longer operations and make it more difficult to remove water formed in the reaction. The temperature is easily controlled when toluene is used as the solvent.

Although the presence of aromatic solvent is not required, it is preferred to have it present in the reaction, the preferred concentration of the reactive components, vinyl aldehyde and compound of Formula (4), in the solution is 60°–80%. While concentrations of less than 50% of those starting matrials tend to favor tend closure to a VDO compound, they are not commercially attractive.

The aliphatic hydrocarbon can be any aliphatic hydrocarbon boiling within the desired range, for example, n-hexane, n-heptane, and cyclohexane, but preferably is petroleum ether having a boiling temperature range of about 60°–100° C.

The catalyst can be an organic acid such as, for example, oxalic acid; or an inorganic acid such as, for example, sulfuric or phosphoric acid. Each of those acids gives an insoluble calcium and/or barium salt and can be precipitated in that form from the reaction medium and removed by filtration. Alternatively, the reaction can be run in the presence of a cationic ion exchange resin, which can be readily removed from the reaction medium without neutralization. For example, according to one embodiment, a fixed bed catalyst can be made from polypropylene pellets coated with NAFION™ fluoropolymer material which provides sulfonic acid.

The reaction is run for about 2 hours at about 80° C. (boiling temperature of petroleum ether/water azeotrope) in the presence of a small amount of an antioxidant such as, for example, hydroquinone. Removal of water as azeotrope drives the reaction to completion. At the conclusion of the reaction, when water is no longer formed, the catalyst is removed by filtration, decantation, or centrifugation. The solvent is then stripped from the liquid phase, and the residue is distilled at a reduced pressure.

This invention is now illustrated by the following examples of certain representative embodiments thereof, where all parts, proportions, and percentages are by weight unless otherwise indicated.

EXAMPLE 1

Equimolar amounts of 97.41 g of trimethylolpropane (TMP) and 40.66 g of acrolein were dissolved in a mixture of 62.5 g of toluene and 62.5 g of petroleum ether boiling within the range of 60°–80° C. To this solution, there was added 0.07 g of hydroquinone (antioxidant) and 2.76 g of oxalic acid (catalyst). The solution was heated from ambient temperature to 70° C., at which point it began refluxing. Heating was continued for a total period of 2.75 hours, while removing petroleum ether/water azeotrope as the overhead. During that time, the temperature of the solution increased to 80°–85° C., where it remained for about 1.5 hours. The amount of water in the azeotrope was 13.76 g, which corresponded to quantitative water recovery (calculated: 13.07 g).

Oxalic acid was neutralized by the addiiton of 2.27 g of calcium hydroxide. The resulting calcium oxalate was removed by filtration; the remaining petroleum ether and the toluene were stripped, and the liquid residue was distilled at a temperature of 149° C. and at a pressure of 1.5 mm Hg (200 Pa). The yield of the VDO product, compound (3), as shown above, was almost quantitative.

EXAMPLE 2

This experiment was carried out under similar conditions starting with 92.6 g of TMP and 38.6 g of acrolein. Oxalic acid, 2.62 g, was the catalyst, and hydroquinone, 0.07 g, was used as antioxidant. In this example, aromatic hydrocarbon solvent was not used, but the amount of petroleum ether was increased to 131.2 g. The temperature was quickly raised to 50° C. and then, gradually, over a period of 3 hours, to 69° C. Water was recovered in an amount of 13.5 g. Mass spectrometric analysis showed that the residue left after removal of volatile material contained a fair amount of unchanged TMP.

EXAMPLE 3

This experiment was carried out in the manner described in Example 1, starting with equimolar amounts of TMP and acrolein, 1198.6 g and 500.24 g, respectively.

Both toluene and petroleum ether (b.p. 60°–80° C.) were used in equal amounts of 283.2 g each. The process thus was run at a 73.8% concentration of reactants. Hydroquinone (0.85 g) and oxalic acid (33.98 g) were added to the solution. The temperature of the solution was raised from 12° C. to 64° C. during a period of 15 minutes and then gradually to 79° C. over a period of 3 hours and 5 minutes. A 72.5% yield of the desired VDO compound was obtained.

Those skilled in the art will no doubt be able to compose numerous variations on the themes disclosed, such as changing the amounts of ingredients insignificantly from those shown, adding innocuous or supplementary substances, or substituting equivalent or analogous components for those shown. Such variations are considered to be within the inventive concept, as defined by the following claims.

I claim:

1. Process for the synthesis of 1,3-dioxo compounds substituted in the 2-position with a vinyl group, said process comprising:

A) selecting a vinyl aldehyde and a compound having at least three hydroxymethyl groups in positions separated by one carbon atom and having no other hydroxyl groups in its molecule, all the hydroxymethyl groups present being structurally equivalent, said compound being represented by the following formula

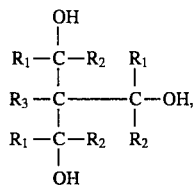

where all $R_1$ groups are concurrently the same meaning and are selected from the group consisting of H, $CH_3$, $CH_2CH_3$, [$CH_2CH_3$,]phenyl, Cl, F, and COOR;

all $R_2$ groups are concurrently the same meaning and are selected from the group consisting of H, $CH_3$, $CH_2CH_3$phenyl, Cl, F, and COOR; and $R_3$ is selected from the group consisting of H, $CH_3$, $CH_2CH_3$, phenyl, Cl, F, and COOR; and R is a $C_1$–$C_{20}$ alkyl or a $C_6$–$C_{10}$ aryl group;

B) contacting together the compounds selected in step A, above, in the presence of an aromatic hydrocarbon solvent having a boiling point of about 100°–115° C., and in the presence of an aliphatic hydrocarbon having a boiling point within the range of about 60–100° C. and being capable of forming a binary azeotrope with water within this temperature range; said aliphatic hydrocarbon being present in an amount of 5–30 weight percent, based on the total of the materials recited in step A above; plus any aromatic hydrocarbon solvent present; and the concentration of the materials selected in step A in the solution being about 50–95 weight percent;

C) refluxing the solution in the presence of a nonvolatile acid catalyst having a $pK_a$ at room temperature in an aqueous medium of less than 5.0, and removing from the solution a binary azeotrope of water with the second, aliphatic hydrocarbon added in step B above, until the reaction is substantially complete;

D) separating the acid catalyst from the liquid phase; and

E) removing any organic liquids present in the liquid phase and recovering the reaction product.

2. The process of claim 1 wherein the starting compound having structurally equivalent hydroxymethyl groups is trimethylolpropane or trimethylolethane.

3. The process of claim 1 wherein an aromatic hydrocarbon solvent is present and is toluene.

4. The process of claim 1 wherein the aliphatic hydrocarbon liquid is petroleum ether having a boiling range of about 60°–80° C.

5. The process of claim 4 wherein toluene is present, and the weight amounts of toluene and petroleum ether are about equal.

6. The process of claim 1 wherein the catalyst is on a fixed bed and is a fluoropolymer material which provides sulfonic acid groups.

* * * * *